(12) United States Patent
Lan et al.

(10) Patent No.: US 7,981,438 B2
(45) Date of Patent: Jul. 19, 2011

(54) USE OF α-MANGOSTIN AS A MOSQUITO LARVICIDE

(75) Inventors: Que Lan, Madison, WI (US); Min-Sik Kim, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 303 days.

(21) Appl. No.: 12/130,134

(22) Filed: May 30, 2008

(65) Prior Publication Data

US 2008/0300300 A1 Dec. 4, 2008

Related U.S. Application Data

(60) Provisional application No. 60/932,269, filed on May 30, 2007.

(51) Int. Cl.
*A01N 25/02* (2006.01)
(52) U.S. Cl. ......................... 424/405; 514/455
(58) Field of Classification Search .................. None
See application file for complete search history.

(56) References Cited

PUBLICATIONS

Wolfram et al Osage Orange Pigments—J. of Organic Chemistry (1964) 29(3), 689-691.*
Ee et al Xanthones From Carcinia Mangostana—Natural Products Research—= Part A (2006), 20(12), pp. 1067-1073.*
Avdulov NA et al., "Lipid binding to sterol carrier protein-2 is inhibited by ethanol," Biochimica et Biophysica Acta, 1999, 1437:37-45.
Canavoso LE et al., "Metabolic pathways for diacylglycerol biosynthesis and release in the midgut of larval *Manduca sexta*.," Insect Biochem Mol Biol., 2000, 30(12):1173-80.
Chanderbhan R et al., Sterol Carrier Protein2: Delivery of cholesterol from adrenal lipid droplets to michchondria for pregnenolone synthesis, J Bio Chem 1982 257(15):8928-893.
Denholm et al., "Insecticide resistance on the move," Science, 2002, 297:2222-2223.
Dyer et al., "The structural determination of an insect sterol carrier protein-2 with a ligand bound C16 fatty acid at 1.35Å resolution," J Biol Chem, 2003, 278:39085-3909.
Elliott M, "Properties and applications of pyrethroids," Environ Health Perspect., 1976, 14:1-2.
Fuchs M et al., "Disruption of the sterol carrier protein 2 gene in mice impairs biliary lipid and hepatic cholesterol metabolism," J Biol Chem, 2001, 276(51):48058-48065.
Gallegos AM et al., "Gene structure, intracellular localization, and functional roles of sterol carrier protein-2," Prog Lipid Res, 2001, 40(6):498-563.
Hopert et al., "Characterization of Estrogenicity of Phytoestrogens in an Endometrial-derived Experimental Model," Environ Health Perspect., 1998, 106(9):581-586.
Jung H et al., "Antioxidant xanthones from the pericarp of *Garcinia mangostana* (Mangosteen)," J. Agric. Food Chem., 2006, 54 (6): 2077-82.
Kim MS et al., "Identification of mosquito sterol carrier protein-2 inhibitors," J Lipid Res., 2005, 46(4):650-657.
Lan Q et al.,"Subcellular localization of mosquito sterol carrier protein-2 and sterol carrier protein-x," J. Lipid Res., 2004, 45(8):1468-1474.

(Continued)

*Primary Examiner* — Neil Levy
(74) *Attorney, Agent, or Firm* — Quarles & Brady LLP

(57) ABSTRACT

Methods of killing mosquito larvae and controlling an adult mosquito population by using α-mangostin, 3,6,8-yrihydroxy-2-methoxy-1,7-bis(3-methylbut-2-enyl)xanthen-9-one, or a salt, solute, hydrate or solvate thereof. Mosquito larvae are killed by contacting a lethal dose of α-mangostin with mosquito larvae. Adult mosquito populations are controlled by treating a mosquito larvae population with a lethal dose of α-mangostin.

4 Claims, 5 Drawing Sheets

PUBLICATIONS

Laphookhieo S et al., "Cytotoxic and antimalarial prenylated xanthones from *Cratoxylum cochinchinense*," Chem Pharm Bull (Tokyo), 2006, 54(5):745-747.

Moncecchi D et al., "Sterol carrier protein-2 expression in mouse L-cell fibroblasts alters cholesterol uptake," Biochim Biophys Acta, 1996, 1302(2):110-116.

Nishiura JT et al., "Modulation of larval nutrition affects midgut neutral lipid storage . . . ," J Insect Physiol., 2007, 53(1):47-58.

Shaneyfelt ME et al., "Natural products that reduce rotavirus infectivity identified by a cell-based moderate-throughput screening assay," Virol J., 2006, 3:68.

Suksamrarn S et al., "Cytotoxic prenylated xanthones from the young fruit of *Garcinia mangostana*," Chem Pharm Bull (Tokyo), 2006, 54(3):301-5.

* cited by examiner

USE OF α-MANGOSTIN AS A MOSQUITO LARVICIDE

CROSS REFERENCE TO RELATED APPLICATIONS

This application claims priority to and benefit of U.S. Provisional Application Ser. No. 60/932,269 filed on May 30, 2007, and is hereby incorporated herein by reference.

This application is related to U.S. patent application Ser. No. 60/874,167 filed on Dec. 11, 2006.

STATEMENT REGARDING GOVERNMENT INTEREST

This invention was made with United States government support awarded by the following agencies: ARMY/SMDC W9113M-05-1-0006 and USDA/CSREES Grant 08-CRHF-0-6055. The United States government has certain rights in this invention.

BACKGROUND OF THE INVENTION

One driver to develop new insecticides has been the desire to replace toxic and irksome insecticides. The notorious DDT was introduced as a safer alternative to the then-used lead and arsenic compounds. When used under the correct conditions, almost any chemical substance is safe. However, when used under the wrong conditions, most insecticides can be a threat to health and/or the environment.

Some insecticides have been banned because that they are persistent toxins that adversely affect animals and/or humans. Dichloro Diphenyl Trichloroethane (DDT) is an example of a widely used (and maybe misused) pesticide. One impact of DDT is that it reduces the thickness of the egg shells from predatory birds. Such shells lack viability due to the thin shell causing reductions in predatory bird populations. DDT and a number of related compounds cause such thin shells due to the process of bioaccumulation.

Bioaccumulation is where the chemical accumulates in fat present in the animals due to the chemical's stability and fat solubility. Also, DDT may bio-magnify, which causes progressively higher concentrations in the body fat of animals farther up the food chain. The near-worldwide ban on agricultural use of DDT and related chemicals has allowed some birds, such as the peregrine falcon, to recover in recent years.

A number of the organochlorine pesticides have been banned for most uses worldwide. Organochlorine pesticides are globally controlled by the Stockholm Convention on Persistent Organic Pollutants. Organochlorine pesticides include: aldrin, chlordane, DDT, dieldrin, endrin, heptachlor, mirex and toxaphene.

The current urgent need for new and effective insecticides stems, in large part, from the fact that many insect pests have become resistant to currently available insecticides. (Denholm et al. 2002, "Insecticide resistance on the move," *Science* 297:2222-2223).

Hence, there exists a tremendous long-felt need for insecticides, pesticides, ovicides and larvicides that are effective against pests, that are non-toxic to animals and humans, and that do not adversely impact the environment or ecosystem.

Sterol carrier protein-2 (SCP-2) is a conserved intracellular sterol carrier protein. (Gallegos A M et al., Gene structure, intracellular localization, and functional roles of sterol carrier protein-2, *Prog Lipid Res* 2001 40(6):498-563). SCP-2 was reported in early literature as related to delivery of cholesterol from preformed stores to and into mitochondria for initiation of steroid hormone synthesis. (Chanderbhan R et al., Sterol Carrier Protein$_2$: Delivery of cholesterol from adrenal lipid droplets to michchondria for pregnenolone synthesis, *J Bio Chem* 1982 257(15):8928-8934). SCP-2 binds lipids in both vertebrate and insect systems, whereby its affinity for cholesterol is much greater than its affinity for fatty acids.

While studying the mosquito sterol carrier protein (AeSCP-2), it has been reported that there exists conversed and divergent functions between vertebrate and invertebrate SCP-2. (Dyer et al., 2003, "The structural determination of an insect sterol carrier protein-2 with a ligand bound C16 fatty acid at 1.35 Å resolution," *J Biol Chem* 278:39085-39091).

Several small molecules have been reported as inhibitors to the mosquito SCP-2, whereby the compounds are also reported to be lethal to both mosquitoes and tobacco hornworms likely due to a reduction in cholesterol uptake, whereby the toxicity of N-(4-{[4-(3,4-dichlorophenyl)-1,3-thiazol-2-yl]amino}phenyl)acetamide in mice has also been reported. (Kim M S et al., Identification of mosquito sterol carrier protein-2 inhibitors, *J Lipid Res* 2005 46(4):650-657). SCP-2 knockouts in mice have been reported to reduce the percentage of cholesterol absorbed in the intestine. (Fuchs M et al., Disruption of the sterol carrier protein 2 gene in mice impairs biliary lipid and hepatic cholesterol metabolism, *J Biol Chem* 276(51):48058-48065).

It has also been reported that ethanol inhibits lipid binding to SCP-2. (Avdulov N A et al., Lipid binding to sterol carrier protein-2 is inhibited by ethanol, *Biochimica et Biophysica Acta* 1999 1437:37-45).

SCP-2 over-expression enhances cholesterol uptake in both mammalian and mosquito cultured cells. (Moncecchi D et al., Sterol carrier protein-2 expression in mouse L-cell fibroblasts alters cholesterol uptake, *Biochim Biophys Acta* 1996 1302(2):110-116; Lan Q et al., 2004, "Subcellular localization of mosquito sterol carrier protein-2 and sterol carrier protein-x, *J. Lipid Res.* 45(8): 1468-1474).).

AeSCP-2 is a mosquito sterol carrier protein-2. Plants and insects have evolved over millions of years. Many plants produce natural compounds that are insecticidal as a mechanism of self-defense. For example, pyrethrin is a natural insecticide produced by certain species of the chrysanthemum plant. (Elliott M, 1976, "Properties and applications of pyrethroids," *Environ Health Perspect.* 14:1-2).

Pyrethroids are synthetic derivatives of pyrethrin. Pyrethroids are widely used insecticides in the developed countries due to low toxicity to vertebrate species and low environmental impact.

It has been reported that α-mangostin has been identified as useful for inhibiting cholesterol-binding in SCP-2 via the high throughput screening method. (Kim M S et al., 2005, "Identification of mosquito sterol carrier protein-2 inhibitors," i J. Lipid Res. 46(4):650-7).

α-Mangostin has been shown to be effective against certain cancer cells even though the mechanism is unknown to date. (Laphookhieo S et al., 2006, Cytotoxic and antimalarial prenylated xanthones from *Cratoxylum cochinchinense*, *Chem Pharm Bull* (Tokyo) 54(5):745-7; and Suksamrarn S et al., 2006, Cytotoxic prenylated xanthones from the young fruit of *Garcinia mangostana*, *Chem Pharm Bull* (Tokyo). 54(3): 301-5). Others have reported that α-Mangostin reduces rotavirus infectivity, however, the mechanism is unknown. (Shaneyfelt M E et al., 2006, Natural products that reduce rotavirus infectivity identified by a cell-based moderate-throughput screening assay, *Virol J.* 3:68).

DESCRIPTION OF DRAWINGS OF THE EXEMPLARY EMBODIMENTS

SUMMARY OF THE INVENTION

Figure 1:
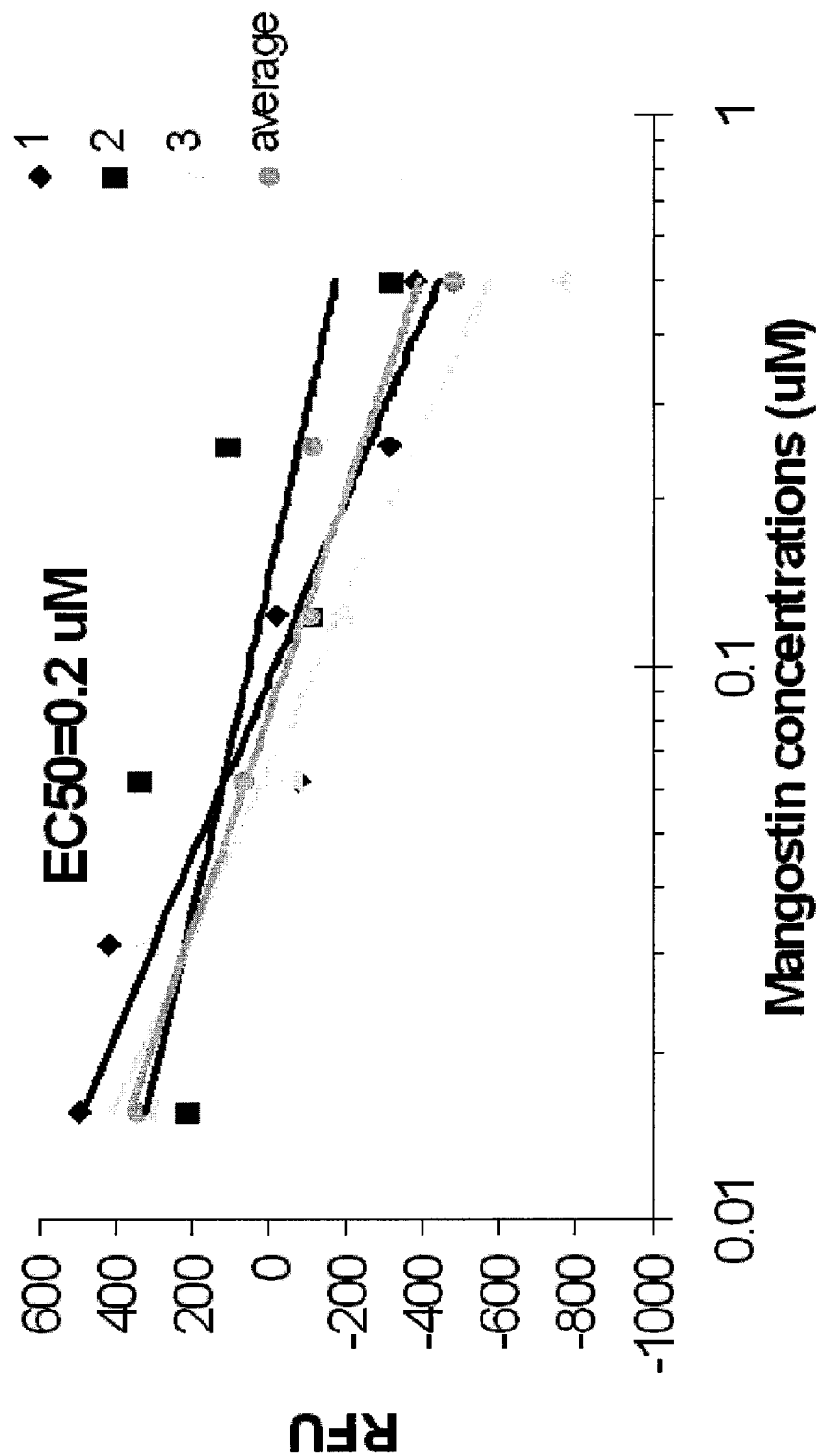
FIG. 1 is a graph showing the inhibitory effect of α-mangostin on NBD-cholesterol binding to recombinant AeSCP-2.

One aspect of the invention is a method of killing mosquito larvae comprising contacting mosquito larvae with a lethal dose of 3,6,8-yrihydroxy-2-methoxy-1,7-bis(3-methylbut-2-enyl)xanthen-9-one according to the formula or a salt, solute, hydrate or solvate thereof.

In an exemplary embodiment of the method, 50% of the lethal dose is in the range of 1.12 to 4.18 ppm.

Another aspect of the invention is a method of controlling an adult mosquito population comprising treating a mosquito larvae population with a lethal dose of 3,6,8-yrihydroxy-2-methoxy-1,7-bis(3-methylbut-2-enyl)xanthen-9-one according to the formula or a salt, solute, hydrate or solvate thereof.

In an exemplary embodiment of the method, 50% of the lethal dose is in the range of 1.12 to 4.18 ppm.

DETAILED DESCRIPTION OF THE EXEMPLARY EMBODIMENTS

As used herein, "salts" of the instant compound may be a salt including, but not limited to, acid addition salts formed by mixing a solution of the instant compound with a solution of a suitable acid. The suitable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. For example, the salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate triethiodide, and other known salts suitable for use with α-mangostin.

As used herein, "hydrates" of the instant compound may be a pharmaceutically suitable (i.e., pharmaceutically acceptable) hydrate is a compound formed by the addition of water or its elements to a host molecule (e.g., the free form version of the compound) including, but not limited to, monohydrates, dihydrates, etc.

As used herein, "solvates" of the instant compound may be a pharmaceutically suitable (i.e., pharmaceutically acceptable) solvate, whereby solvation is an interaction of a solute with the solvent which leads to stabilization of the solute species in the solution, and whereby the solvated state is an ion in a solution complexed by solvent molecules. Mangostin is a natural organic compound isolated from various parts of the mangosteen tree (*Garcinia mangostana*). It is a yellow crystalline solid with a xanthone core structure. α-Mangostin and a variety of other xanthones from mangosteen have been investigated for biological properties including antioxidant, anti-bacterial, anti-inflammatory, and anticancer activities. (Jung H et al., 2006, "Antioxidant xanthones from the pericarp of *Garcinia mangostana* (Mangosteen)," *J. Agric. Food Chem.* 54 (6): 2077-82).

α-Mangostin has a melting point of 182° C. (360° F.). α-Mangostin has a molecular weight of 410.460, and it has the following structure:

The IUPAC name for α-mangostin is 3,6,8-Trihydroxy-2-methoxy-1,7-bis(3-methylbut-2-enyl)xanthen-9-one and the chemical formula is $C_{24}H_{26}O_6$.

EXAMPLES

Example 1

At 0.1 mM concentration, α-mangostin decreased NBD-cholesterol binding to AeSCP-2 by 23-29%. As shown in FIG.

1, data generated from in vitro competition binding assays demonstrate that the $IC_{50}$ of α-mangostin is 0.2 μM, which is lower than that of SCPI-1. Specifically, FIG. 1 illustrates the inhibitory effect of α-mangostin on NBD-cholesterol binding to recombinant AeSCP-2. RFU=relative NBD-cholesterol fluorescent unit normalized with NBD-cholesterol background readings. The assays that were used included 5 μM NBD-cholesterol+5 uM AeSCP-2+increasing concentrations of α-mangostin in 10 uM potassium phosphate buffer (pH 7.4).

Biological activities of α-mangostin were examined in mosquito larvae. As shown in Table 1, α-mangostin is a potent mosquito larvicide that has lower $LD_{50}$ than SCPI-1. α-Mangostin outperformed SCPI-1 (a synthetic compound) in both the $1^{st}$ and $4^{th}$ larval stages, which indicates that α-mangostin is an unexpectedly superior and significantly more potent larvicide.

TABLE 1

TOXICITY ASSESSMENTS OF NATURAL COMPOUNDS

| compound | $LD_{50}$ (uM) in $1^{st}$ instar | $LD_{50}$ (uM) in $4^{th}$ instar |
|---|---|---|
| DMSO (negative control) | ND | ND |
| SCPI-1 (positive control) | 4.21 ± 0.38 (or, 1.93 ppm) | 24.04 ± 4.16 (or, 11.04 ppm) |
| α-mangostin | 2.73 ± 2.46 (or, 1.12 ppm) | 10.18 ± 1.49 (or, 4.18 ppm) |
| obtusauione | 6.36 ± 1.70 (1.62 ppm) | ND |
| isoginkgetin | 11.29 ± 3.00 (6.60 ppm) | ND |
| lonchocarpic acid | 11.99 ± 1.93 (5.21 ppm) | ND |

ND = not determined due to very low mortality.

Compound was tested at concentrations within the range of 0.65-25.00 μM. Each assay included 60 larvae ($1^{st}$ instar or $4^{th}$ instar) in 60 ml dd$H_2O$ containing either compound or control agent, mortality was recorded until 90% adult emerge rate. The percentage of mortality was transformed into Probit value and plotted against concentration to determine the $LD_{50}$ value. Each assay was repeated at least three times with different batches of larvae. The mean and standard deviation values are listed above. ND=not determined due to very low mortality.

Compounds were tested at concentrations within the range of 0.65-25.00 μM. Each assay included 60 larvae ($1^{st}$ instar or $4^{th}$ instar) in 60 ml dd$H_2O$ containing either compound or control agent. Mortality was recorded until 90% adult emerge rate. The percentage of mortality was transformed into Probit value and plotted against concentrations to determine the $LD_{50}$ value. Each assay was repeated at least three times with different batches of larvae. The mean and standard deviation values are shown in Table 1.

The mode of action for α-mangostin was examined by looking at the neutral lipid levels in the midgut tissue. In insect larvae, the midgut tissue converts absorbed free fatty acid to triglycerides and cholesterol to cholesterol esters (i.e., neutral lipids), respectively, in the endoplasmic reticulum. Then, triglycerides are exported out of the midgut epithelium as diglycerides after cleavage by a lipase. (Canavoso L E et al., 2000, "Metabolic pathways for diacylglycerol biosynthesis and release in the midgut of larval *Manduca sexta*," *Insect Biochem Mol Biol.* 30(12):1173-80).

Therefore, triglycerides accumulate in the midgut in feeding larvae. In mosquito larvae, neutral lipids are completely depleted after the metamorphic commitment in late $4^{th}$ instars, when active feed has stopped. (Nishiura J T et al., 2007, "Modulation of larval nutrition affects midgut neutral lipid storage and temporal pattern of transcription factor expression during mosquito metamorphosis," *J Insect Physiol.* 53(1):47-58).

Figure 2:
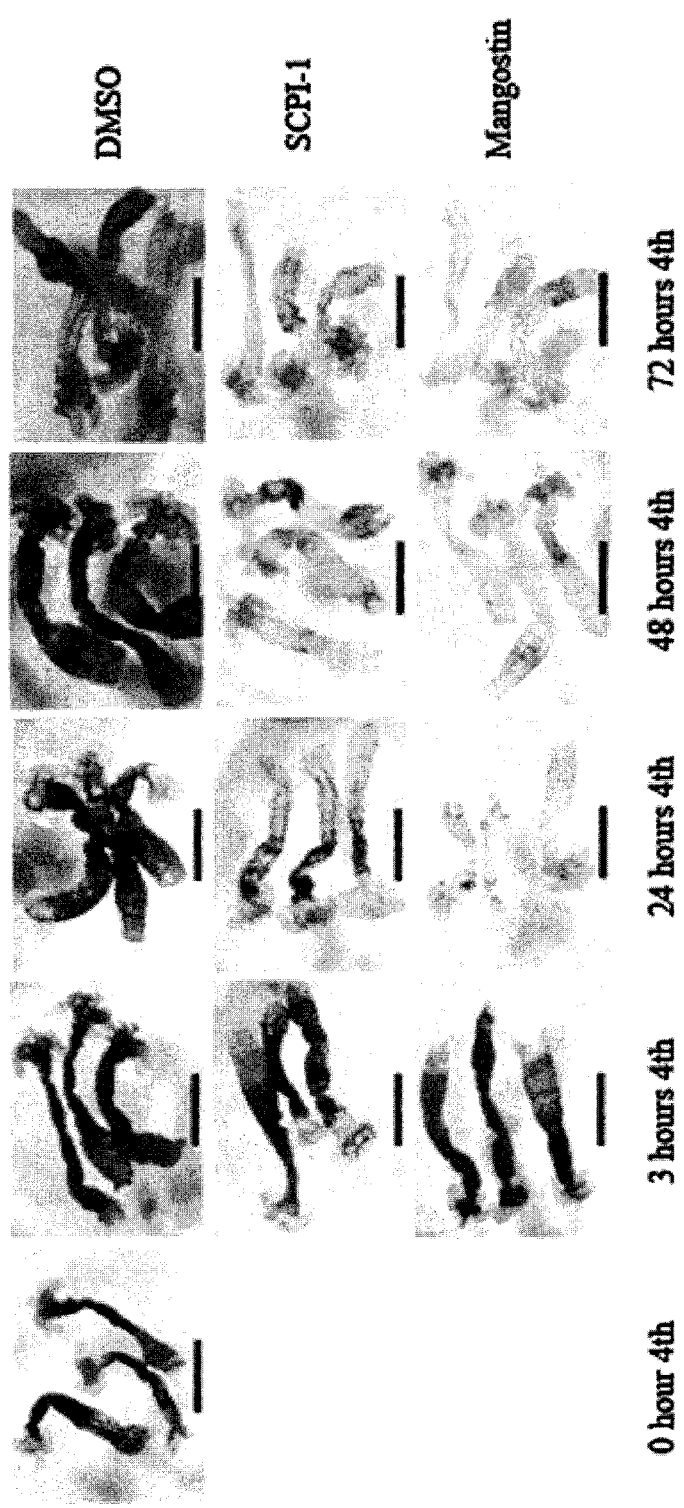
FIG. 2 shows various series of pictures showing the effect of α-mangostain on neutral lipid levels in the midgut of 4th instar larvae, whereby SCPI-1 is N-(4-{[4-(3,4-dichlorophenyl)-1,3-thiazol-2-yl]amino}phenyl)acetamide hydrobromide, and whereby DMSO is dimethyl sulfoxide.

As shown in FIG. 2, in DMSO-treated larvae, neutral lipids were depleted in 72 hour-old $4^{th}$ instar larvae, which is immediately before pupation (i.e., larval-pupal molt). In SCPI-1 treated larvae, about ½ of neutral lipids were depleted in 24 hour-old larvae. Without being bound to any particular theory, it indicates that SCPI-1 severely impaired the fatty acid or cholesterol metabolism in the midgut by either blocking the synthesis of triglycerides from free fatty acid or by accelerating the exportation of triglyceride out of the midgut or blocking the synthesis of cholesterol esters from cholesterol or accelerate the export of cholesterol esters.

The series of pictures shown in FIG. 2 demonstrate the effect of α-mangostain on neutral lipid levels in the midgut of 4th instar larvae. The newly molted 4th instar larvae were treated with DMSO (the negative control), 25 μM SCPI-1 (the positive control), and 10 μM α-mangostin. The midgut tissue was dissected out at the indicated point in time after treatment initiation. The dissected treated midgut tissue was stained with Red Oil O for neutral lipids in situ.

Preliminary data suggest that the effect of SCPI-1 on neutral lipid levels in the larval midgut is most likely via blockage of triglycerides synthesis due the impairment in free fatty acid transport mediated by AeSCP-2 (data not shown).

In larvae treated with α-mangostin, there were scant amounts of neutral lipids in the midgut after 24 hours treatment, which indicates a more severe effect compared to SCPI-1 on neutral lipids accumulation in the midgut. The results from neutral lipid assays are consistent with the observation that α-mangostin is more potent than that of SCPI-1 in killing mosquito larvae. (See Table 1). SCPI-1 is N-(4-{[4-(3,4-dichlorophenyl)-1,3-thiazol-2-yl]amino}phenyl)acetamide hydrobromide, and the structure is

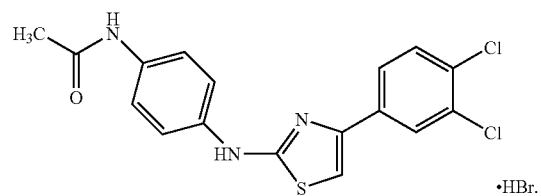

Figure 3:
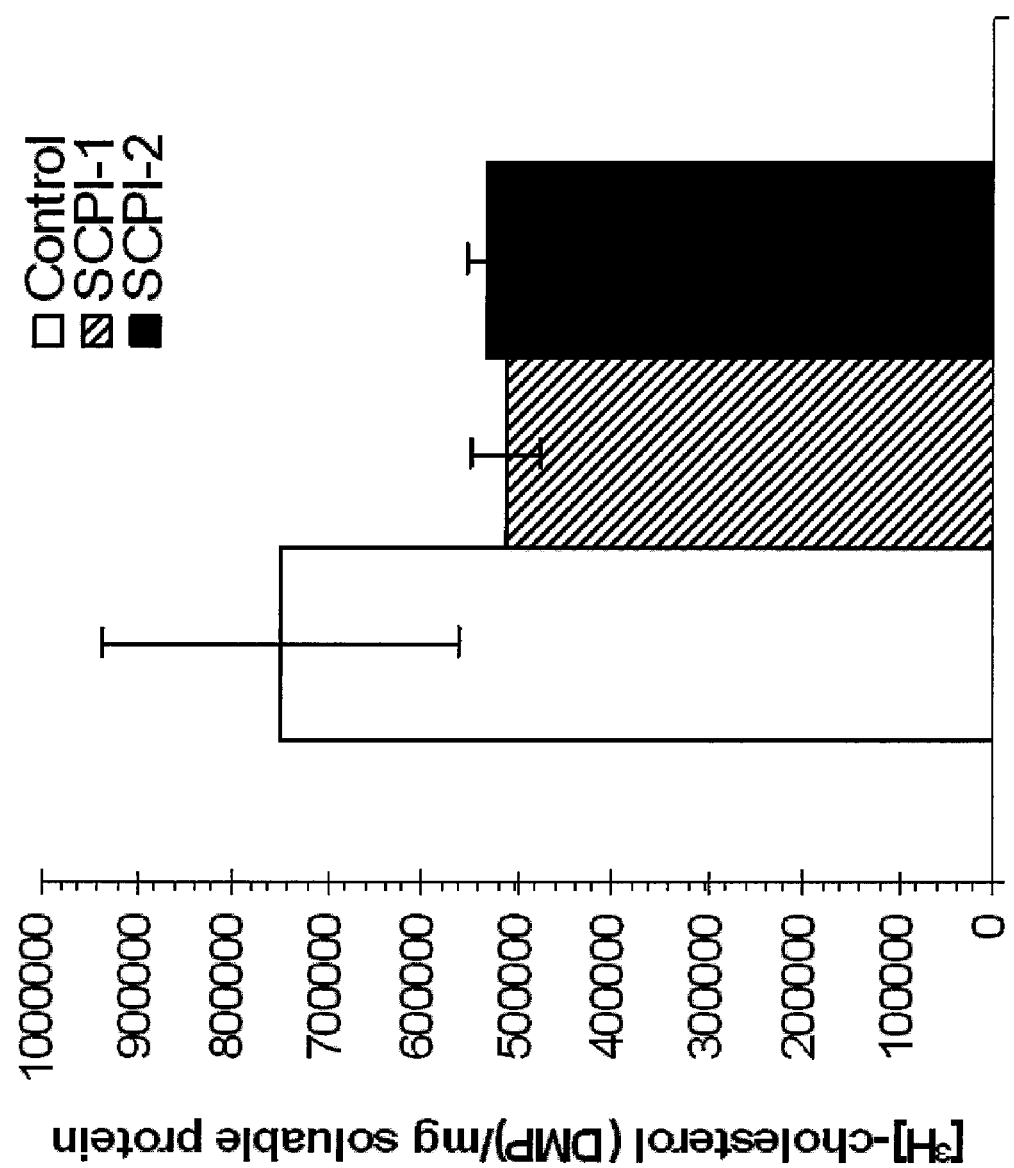
FIG. 3 is a bar graph showing the effect of SCPI treatment on accumulation of [$^3$H]-cholesterol in mosquito 4th instar larvae, whereby SCPI-2 is 8-chloro-2-(3-methoxyphenyl)-4,4-dimethyl-4,5-dihydroisothiazolo[5,4-c]quinoline-1(2H)-thione, and whereby the control is DMSO.
Figure 4:
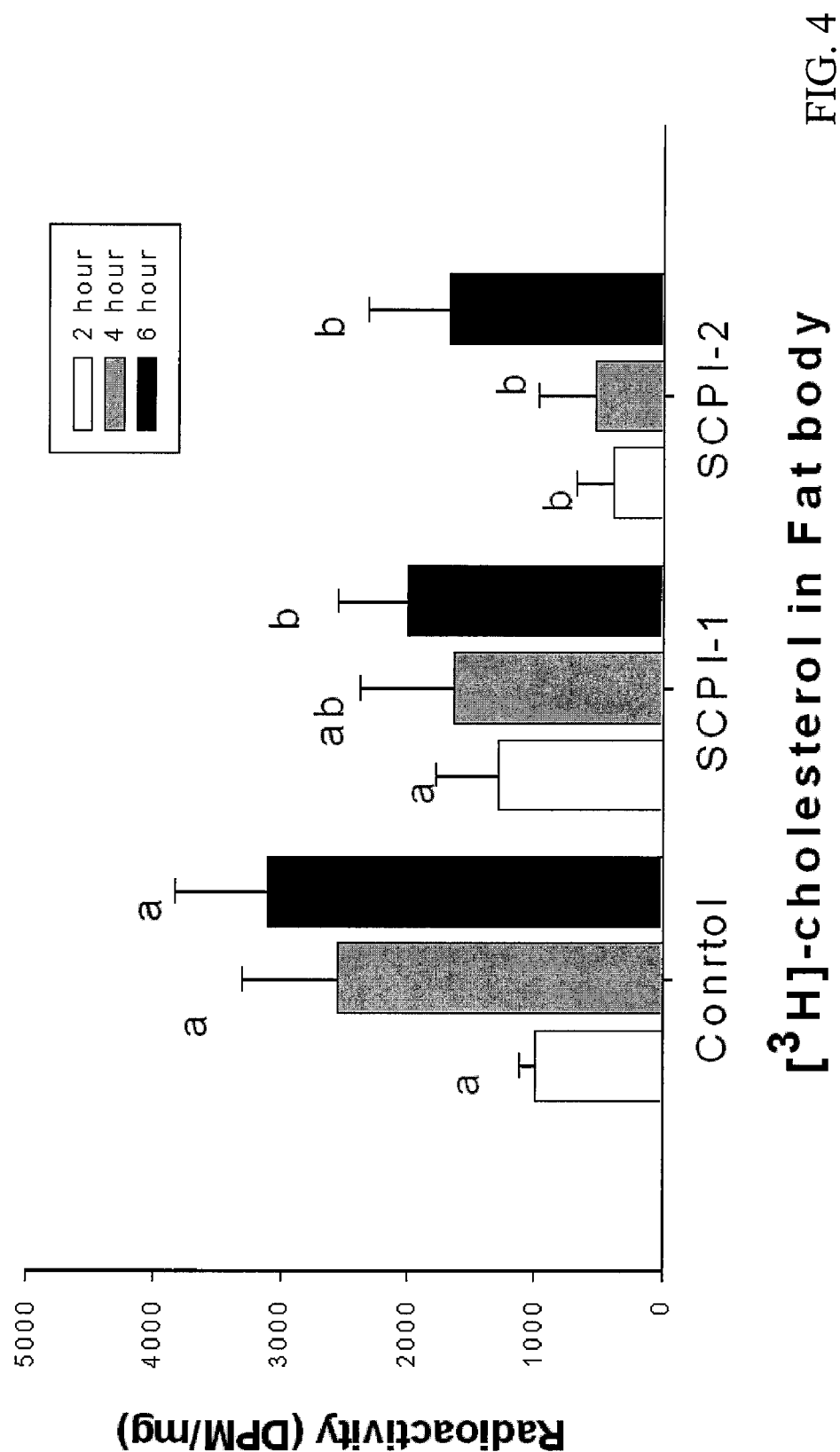
FIG. 4 is a bar graph showing the effects of various SCPIs on cholesterol uptake in *M. sexta* Day 1 5th instar larvae, whereby the control is DMSO.

As shown in FIGS. 3 and 4, SCPIs reduce cholesterol uptake in mosquito and *Manduca* larvae. α-Mangostin may also have similar effects on cholesterol absorption. Without being bound to any theory, it is hypothesized that the mode of action (in general) for α-mangostin and SCPIs involves inhibiting the intracellular transport of lipids (i.e., free fatty acid and cholesterol), which directly affects lipid metabolisms in the organism. SCPI-2 is 8-chloro-2-(3-methoxyphenyl)-4,4-dimethyl-4,5-dihydroisothiazolo[5,4-c]quinoline-1(2H)-thione according to the formula

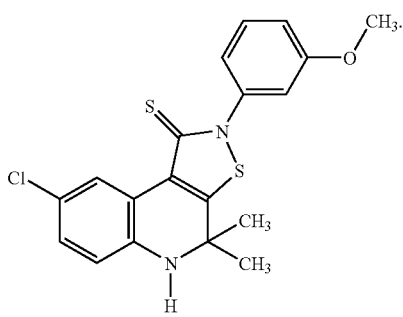

FIG. 3 illustrates the effect of SCPI treatment on accumulation of [$^3$H]-cholesterol in mosquito 4th instar larvae. SCPI-treated 4th instar larvae were labeled with [$^3$H]-cholesterol for 24 hours. The amount of absorbed [$^3$H]-cholesterol was measured. Blank=controls, Hatched=SCPI-1 treated, Black=SCPI-2 treated, and Bar=mean±S.D. (N=5).

FIG. 4 is a bar graph showing the effects of various SCPIs on cholesterol uptake in *M. sexta* Day 1 5th instar larvae. The accumulation of stored [1,2-$^3$H (N)]-cholesterol in the fat body is shown. *M. sexta* early 4th instar larvae (12 insects (4 insects/time)/group) were fasted for 2 hr and then were fed a small piece of diet (0.1 g) containing SCPIs at LD$_{50}$ dosage in 2 μl ethanol and [$^3$H]-cholesterol (0.033 μCi/1 ml ethanol). The control group of larvae were fed a small piece of diet (0.1 g) containing only 2 ul of ethanol and [$^3$H]-cholesterol (0.033 μCi/1 ml ethanol). Larvae that consumed the diet completely within 30 minutes were selected for experiments. In the control and treated groups, the fat body from each individual larva was collected at 2, 4, and 6 hours after feeding. Data was analyzed with two-way ANOVA (GLM procedure) to determine if significant differences existed between the control group and SCPIs treated groups differ significantly. Values=mean±S.D. (N=4).

α-Mangostin can be extracted from the hull of the fruit of the mangosteen tree (*Garcinia mangostana*). α-Mangostin was suspected as a putative phytoestrogen due to the chemical structure similarity to known phytoestrogens. However, α-mangostin does not induce reproductive side effects in mammals like that of phytoestrogens, which was measured by the effect on the formation of complement C3 in mode system. (Hopert A-C et al., 1998, *Environ Health Perspect.* 106(9):581-6 and FIG. 5).

Figure 5:
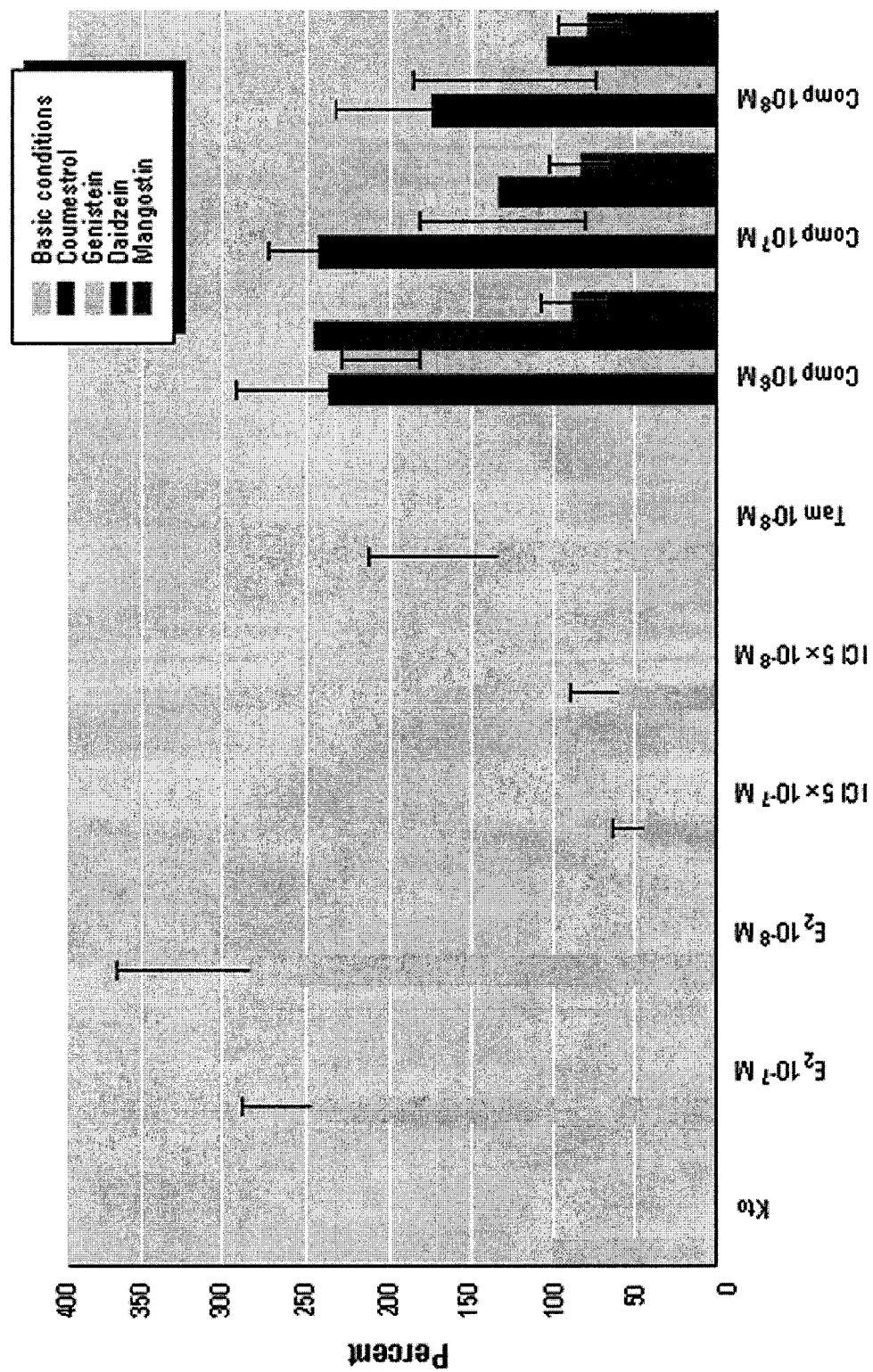
FIG. 5 is a bar graph showing the effect of various compounds to promote the increased production of complement C3. (Hopert et al., 1998, *Environ Health Perspect.* 106(9): 581-586).

FIG. 5 shows the effect of various compounds to promote the increased production of complement C3, which is a well known estradiol-regulated protein of the rat endometrium. Kto=untreated, E2=17β-estradiol, ICI=estrogen antagonist ICI 164384, and Tam=tamoxifen.

We claim:

1. A method of killing mosquito larvae comprising contacting mosquito larvae with a lethal dose of 3,6,8-yrihydroxy-2-methoxy-1,7-bis(3-methylbut-2-enyl)xanthen-9-one according to the formula

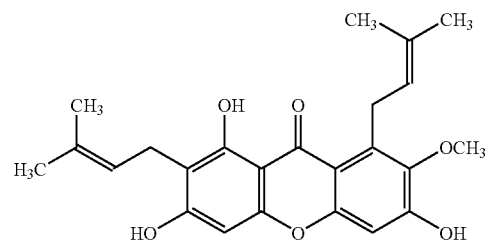

or a salt, solute, hydrate or solvate thereof.

2. The method of claim 1, wherein 50% of the lethal dose is in the range of 1.12 to 4.18 ppm.

3. A method of controlling an adult mosquito population comprising treating a mosquito larvae population with a lethal dose of 3,6,8-yrihydroxy-2-methoxy-1,7-bis(3-methylbut-2-enyl)xanthen-9-one according to the formula

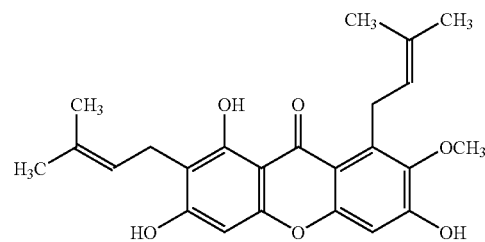

or a salt, solute, hydrate or solvate thereof.

4. The method of claim 3, wherein 50% of the lethal dose is in the range of 1.12 to 4.18 ppm.

* * * * *